United States Patent [19]

Yasuda et al.

[11] 4,423,215
[45] Dec. 27, 1983

[54] METHOD OF PREPARING SODIUM SALTS OF IMIDAZOLEDICARBOXYLIC ACID SUBSTITUTED CEPHALOSPORIN DERIVATIVES

[75] Inventors: Naohiko Yasuda, Yokosuka; Hisao Iwagami, Kawasaki; Yasuo Irie, Kawasaki; Eiji Nakanishi, Kawasaki; Hideomi Saito, Sagamihara, all of Japan

[73] Assignee: Ajinomoto Company, Inc., Tokyo, Japan

[21] Appl. No.: 353,809

[22] Filed: Mar. 2, 1982

[30] Foreign Application Priority Data

Mar. 2, 1981 [JP] Japan .................................. 56-29541

[51] Int. Cl.³ .......................................... C07D 501/38
[52] U.S. Cl. .................................... 544/025; 424/246
[58] Field of Search .......................... 544/25, 26, 27; 424/246

[56] References Cited

U.S. PATENT DOCUMENTS 4,217,450  8/1980  Yasuda et al. ........................ 544/25
4,258,041  3/1981  O'Callaghan et al. ................ 544/25

FOREIGN PATENT DOCUMENTS 55-76887  6/1980  Japan .

Primary Examiner—Nicholas S. Rizzo
Attorney, Agent, or Firm—Oblon, Fisher, Spivak, McClelland & Maier

[57] ABSTRACT

A method of preparing sodium salts of an imidazoledicarboxylic acid derivative of a substituted cephalosporin represented by the general formula of

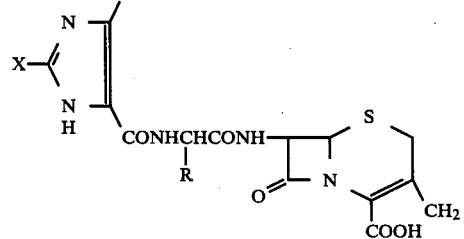

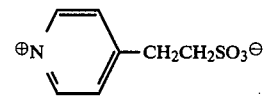

where
X is a radical selected from the group consisting of hydrogen, halogen, hydroxyl, alkyl, aryl, aralkyl, alkoxy, aryloxy, aralkyloxy, mercapto, alkylthio, arylthio, aralkylthio, alkylsulfonyl, arylsulfonyl, aralkylsulfonyl, alkylsulfinyl, arylsulfinyl, aralkylsulfinyl, amino, mono- or dialkylamino, mono- or diarylamino, mono- or diaralkylamino, acylamino, sulfonic acid, nitro or heterocyclic group;
and where R is a radical selected from hydrogen, an organic radical such as alkyl, aryl or aralkyl or a heterocyclic group, said organic radical and heterocyclic group being optionally substituted;
said method comprising reacting a compound represented by the following formula:

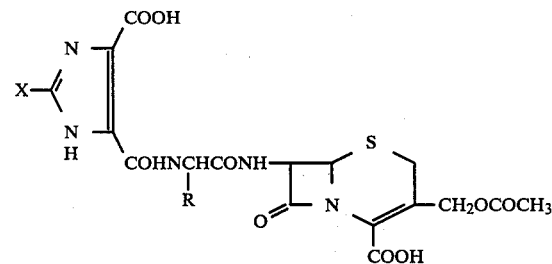

with 4-pyridineethanesulfonic acid in an aqueous solution of sodium iodide and subsequently recovering the salt.

The compounds are useful in the treatment of bacterial infections, particularly *Pseudomonas aeruginosa*, in man and other animals.

2 Claims, No Drawings

METHOD OF PREPARING SODIUM SALTS OF IMIDAZOLEDICARBOXYLIC ACID SUBSTITUTED CEPHALOSPORIN DERIVATIVES

BACKGROUND OF THE INVENTION

1. Field of the Invention

The present invention relates to methods for preparing sodium salts of imidazoledicarboxylic acid derivatives of substituted cephalosporin.

2. Description of the Prior Art

In the specification of laid-open Japanese Patent Application No. 55-76887, salts of imidazoledicarboxylic acid derivatives represented by the following general formula:

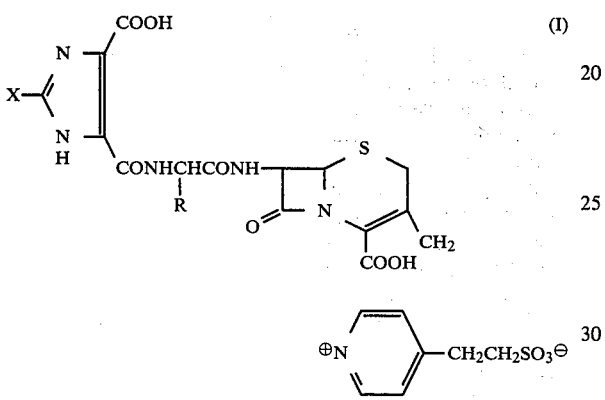

are disclosed which demonstrate antibacterial properties, particularly against *Pseudomonas aeruginosa*, and are useful as antibiotics. The synthesis of the salts involves reacting compounds of the following formula

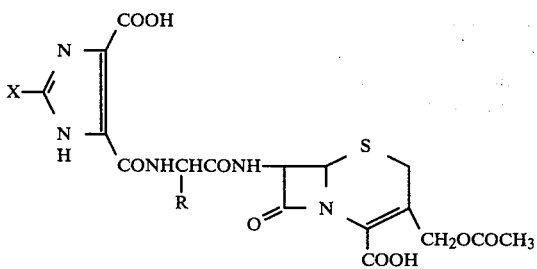

with 4-pyridineethanesulfonic acid in the presence of potassium iodide or potassium thiocyanate in order to introduce pyridinium groups. This reaction results in the formation of the potassium salt of compound (I). Refer to The Journal of Antibiotics, 29, 928 (1976).

It is also disclosed in laid open Japanese Application No. 55-76887, mentioned above, that the sodium salts of the imidazolidicarboxylic acid derivatives (I) are obtained by treating their potassium salt counterparts with ion exchange resin and then neutralizing with aqueous sodium hydroxide solution. This step is both complicated and results in a low yield of final product. Additionally since large amounts of potassium iodide or potassium thiocyanate are used in the reaction, separation of the unreacted iodide salt from the imidazoledicarboxylic acid salt is both difficult and expensive, requiring large quantities of synthesized absorbent such as "Amberlite XAD-2", available from Rohm, and Haas Company.

Thus a need has continued to exist for an improved method of preparing the sodium salts of imidazoledicarboxylic acid derivatives of substituted cephalosporins.

SUMMARY OF THE INVENTION

It is an object of the present invention to provide an improved method of preparing sodium salts of imidazoledicarboxylic acid derivatives of substituted cephalosporins represented by the following formula

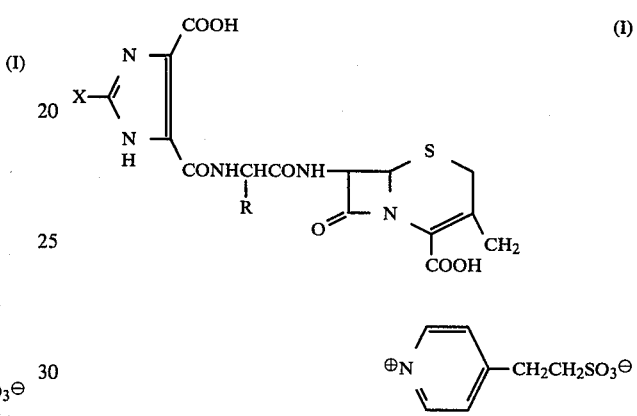

where

X is a radical selected from the group consisting of hydrogen, halogen, hydroxyl, alkyl, aryl, aralkyl, alkoxy, aryloxy, aralkyloxy, mercapto, alkylthio, arylthio, aralkylthio, alkylsulfonyl, arylsulfonyl, aralkylsulfonyl, alkylsulfinyl, arylsulfinyl, aralkylsulfinyl, amino, mono- or dialkylamino, mono- or diarylamino, mono- or diaralkylamino, acylamino, sulfonic acid, nitro or heterocyclic group;

and where R is a radical selected from the group consisting of hydrogen, and an organic radical such as alkyl, aryl or aralkyl or a heterocyclic group, said organic radical or heterocyclic group being optionally substituted.

It is a further object of the present invention to provide an improved method of preparing sodium salts of (I) wherein the sodium salt is prepared directly.

It is a further object of the present invention to prepare sodium salts of (I) wherein satisfactory yield of product is obtained.

It is a further object of the present invention to develop an improved method of treatment for bacterial infections, especially *Pseudomonas aeruginosa*, in man and other mammals.

These and other objects of the invention as will hereinafter become more readily apparent have been attained by reacting a compound represented by the formula

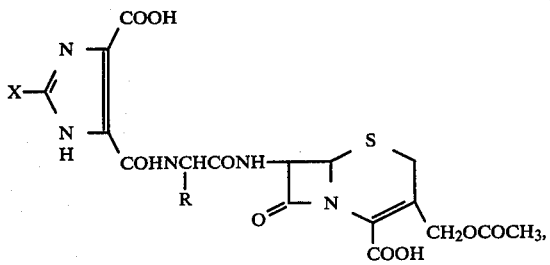

(II)

wherein X and R are as described above, with 4-pyridineethanesulfonic acid in the presence of an aqueous solution of sodium iodide and subsequently separating the sodium salts of imidazoledicarboxylic acid derivatives of substituted cephalosporins as set out in (I).

DETAILED DESCRIPTION OF THE PREFERRED EMBODIMENT

In the above and subsequent descriptions of this specification, suitable examples and illustrations of the various definitions which this invention intends to include within its scope are explained in detail as follows:

"alkyl" may include the $C_1-C_6$ alkyls, straight chained or branched. Suitable alkyl groups may be methyl, ethyl, propyl, isopropyl, butyl, isobutyl, t-butyl, pentyl, hexyl, and the like;

"aryl" may include the $C_6-C_{10}$ aryls. Suitable aryl groups are phenyl, naphthyl, o-methylphenyl, p-methylphenyl, 3,5-dimethylphenyl, o-butylphenyl and the like;

"aralkyl" may include $C_7-C_{10}$ aralkyl groups and may be phenylmethyl, 2-phenylethyl, 2-methyl-3-phenylpropyl, 4-phenylbutyl and the like;

"alkoxy" may include $C_1-C_6$ alkoxy groups and maybe methoxy, ethoxy, propoxy, butoxy, t-butoxy, pentyloxy, hexyloxy and the like;

"aryloxy" may include $C_6-C_{10}$ aryloxy and may be phenoxy, naphthoxy, 1-methoxy-2-naphthoxy, 3,5-dimethyl phenoxy, 4-butylphenoxy and the like;

"aralkyloxy" may include the $C_7-C_{10}$ aralkyloxy groups and may be phenylmethoxy, phenylethoxy, phenylpropoxy, 2-methyl-3-phenyl-propoxy, 4-phenylbutoxy and the like;

"alkylthio" may include the $C_1-C_6$ alkylthio groups and may be methylthio, ethylthio, isopropylthio, t-butylthio, pentylthio and the like;

"arylthio" may include the $C_6-C_{10}$ arylthio groups and may be phenylthio, naphthylthio, p-methylphenylthio, 3,5-dimethylphenylthio and the like;

"aralkylthio" may include the $C_7-C_{10}$ aralkylthio groups and may include phenylmethylthio, phenylethylthio, phenylpropylthio, 2-methyl-3-phenylpropylthio and the like;

"alkylsulfonyl" may include the $C_1-C_6$ alkylsulfonyl groups and may be methylsulfonyl, ethylsulfonyl, isopropylsulfonyl, t-butylsulfonyl and the like;

"arylsulfonyl" may include the $C_6-C_{10}$ arylsulfonyl groups and may be phenylsulfonyl, naphthylsulfonyl, methylphenylsulfonyl, 3,5-dimethylphenylsulfonyl and the like;

"aralkylsulfonyl" may include the $C_7-C_{10}$ aralkylsulfonyl groups and may be phenylmethylsulfonyl, phenylethylsulfonyl, phenylbutylsulfonyl and the like;

"alkylsulfinyl" may include the $C_1-C_6$-alkylsulfinyls and may be methylsulfinyl, ethylsulfinyl, isopropylsulfinyl, t-butylsulfinyl and the like;

"arylsulfinyl" may include the $C_6-C_{10}$ arylsulfinyl groups and may include phenylsulfinyl, naphthylsulfinyl, methylphenylsulfinyl, 3,5-dimethylsulfinyl and the like;

"aralkylsulfinyl" may include the $C_7-C_{10}$ aralkylsulfinyl groups and may include phenylmethylsulfinyl, phenylethylsulfinyl, phenylbutylsulfinyl and the like;

"mono- or dialkylamino" may include the $C_1-C_{12}$ mono- or dialkylamino- groups and may be methylamino, dimethylamino, ethylamino, ethylpropylamino- and the like;

"mono- and diarylamino" groups may include and may be phenylamino, diphenylamino, methylphenylamino, dimethylphenylamino and the like;

"mono- and diaralkylamino" may include the $C_7-C_{20}$ mono- or diaralkylamino groups and may be phenylmethylamino, diphenylmethylamino, N-phenylmethyl-N-phenylethylamino and the like;

"acylamino" may include the $C_1-C_6$ acylamino groups and may be acetylamino, propionylamino, butyrylamino and the like.

"hetero-ring-containing" may include 5-7 member heterocyclic groups and may include pyrolidino, morpholino, piperidino, pyridino and the like. These heterocyclic groups may be substituted with, for example, halogen or $C_1-C_4$ alkyl groups.

The amino-acid portion of the imidazole dicarboxylic acid derivatives may be for example phenylglycine or 4-hydroxyphenyl glycine, in the L-, D- or DL-form. In many cases the D-form is preferred as a result of their higher antibacterial activity.

The imidazole dicarboxylic acid derivatives of the present invention have effective antibacterial activity against not only gram positive and gram negative bacteria but also against *Pseudomonas aeruginosa*. They therefore have a very broad spectrum antibacterial activity and are useful as antibiotics or intermediates thereof for man and other mammals.

It has been found that sodium salt derivatives, wherein the carboxyl groups substituted at the imidazole ring or cephalosporin nucleus or both are converted to sodium salts, demonstrate significantly lower toxicity as compared to their potassium counterparts. See Table 1 below.

TABLE 1

| Acute toxicity of 7B-[D—(—)-α-(4-carboxyimidazole-5-carboxyamide)-phenylacetamide]-3-(4-β-sulfoethyl-pyridinium)-methyl-3-cepham-4-carboxylic acid, disodium salt | |
|---|---|
| | LD$_{50}$(mouse, i.v.) |
| disodium salt | more than 3 g/kg |
| dipotassium salt | 0.5–1 g/kg |

According to the present invention, the sodium salt is obtained directly and the step in the prior art of obtaining the sodium salt by cation exchange of the potassium salt becomes superfluous.

Another advantage of the present invention over the conventional methods which use potassium iodide or potassium thiocyanate is that the reaction product, the sodium salts of the imidazoledicarboxylic acid derivatives of substituted cephalosporins, can be precipitated by introducing the reaction mixture into a hydrophilic organic solvent in which sodium iodide is soluble, and in which the salts precipitate, such as an alcohol of 1–4 carbon atoms, acetone, acetonitrile or mixtures thereof. Thus the precipitated product may be recovered in a purified form and with substantially improved yield.

The reaction is preferably carried out by using sodium iodide as a catalyst in an aqueous solution with a pH of 6.0–7.5. The reaction temperature is preferably maintained at 55°–75° C. and the time required for the reaction to go to completion is normally in the range of 1–2 hours. The reaction requires 10–50 equivalent weights of sodium iodide catalyst for each equivalent weight of product formed.

Upon completion of the reaction, the product may be recovered by addition of the reaction medium contents into a hydrophilic organic solvent which is also a solvent for the excess NaI still unreacted in the medium. Suitable solvents are, among others, acetone, methanol, ethanol, isopropanol, butanol, acetonitrile or mixtures thereof. The product may be further purified by repeated washings with the above-mentioned solvents. Alternatively, the product may be further purified by methods well known in the art, such as column chromatography, recrystallization, etc.

Having now generally described this invention, the same will be better understood by reference to the following specific examples, which are included for purposes of illustration only and are not intended to be limiting thereof.

EXAMPLE 1

16.3 g (30 mM) of 7β-[D-(−)-α-(4-carboxyimidazole-5-carboxamido)phenylacetamido]-cephalosporanic acid and 11.2 g (60 mM) of 4-pyridineethanesulfonic acid are suspended in 70 ml of water, and dissolved in 2 N aqueous solution of sodium hydroxide by adjusting the pH value of the solution to 6.5. After adding 200 g of sodium iodide, the mixture is reacted for 70 minutes at 65° C. while stirring. After the reaction liquid is cooled, it is added dropwise to 750 ml of acetone while being ice cooled and stirred. After cooling overnight, the precipitated solid is filtered off, dissolved again in 75 ml of water, added dropwise to 350 ml of acetone and precipitated in solid form. The precipitated solid is filtered off, dissolved in 75 ml of water, added dropwise to 450 ml of ethanol while being ice cooled and stirred. After cooling again overnight, the precipitated solid is filtered off and dried to obtain 16 g of the desired product.

The thus obtained product is then dissolved in 40 ml of water and its pH value adjusted to 4. This is adsorbed by a column consisting of 700 ml of adsorbent "XAD-2" and the product is eluted in 5% aqueous methanol. The fraction containing the product, still in solution, is concentrated until the volume becomes 160 ml. The pH value of the solution is adjusted to 4, and the solution is then added dropwise to 800 ml of ethanol while being ice-cooled and stirred to precipitate the solid. After cooling overnight, the precipitate is filtered off, and freeze-dried to obtain 6 g of 7β-[D-(−)-α-(4-carboxyimidazole-5-carboxyamido)phenylacetamido]-3-(4-β-sulfoethylpyridinium)-methyl-3-cephen-4-carboxylic acid ·1.5 Na salt·5 hydrate.

ELEMENTAL ANALYSIS

Measured values: C 42.23%, H 4.43%, n 10.58%, S 7.62%, Na 4.37%.

Calculated values based on: $C_{28}H_{24.5}N_6O_{10}S_2 \cdot 3Na_{1.5} \cdot 5H_2O$ C 42.38%, H 4.37%, N 10.59% S 8.08%, Na 4.35%.

| NMR spectrum (Solvent D₂O) |
| --- |
| δ 3.20 (d.d.2H) (2 position > CH₂) |
| δ 3.45 (S.4H) (N 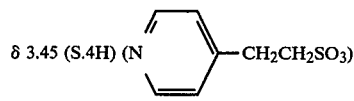 —CH₂CH₂SO₃) |
| δ 5.05 (d.1H) (6 position - H) |
| δ 5.40 (d.d.2H) (3 position - CH₂—N 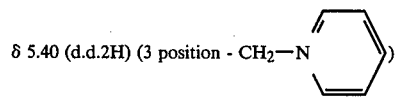) |
| δ 5.65 (S.1H) (—CH—) 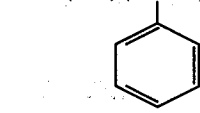 |
| δ 7.50 (m.5H) (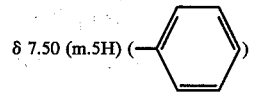) |
| δ 5.80 (d.1H) (7 position - H) |
| δ 8.00 (d. 2H) (pyridine ring 3.5 position-H) |
| δ 8.70 (s. 1H) (imidazole 2 position-H) |
| δ 8.85 (d.2H) (pyridine ring 2.6 position-H) |

EXAMPLE 2

1.1 g (2 mM) of 7β-[D-(−)-α-(4-carboximidazole-5-carboxyamido)-p-hydroxyphenylacetamido]-cephalosporanic acid and 0.75 g (4 mM) of 4-pyridineethanesulfonic acid are suspended in 10 ml of water, and dissolved in aqueous solution of 2 N sodium hydroxide by adjusting the pH value of the said solution to 7.0. After adding 8 g of sodium iodide thereto, it is reacted for 2 hours at 70° C. while stirring. The desired product is then isolated and refined in the manner similar to that described in Example 1, and 0.16 g of 7β-[D-(−)-α-(4-carboxyimidazole-5-carboxyamido)-p-hydroxyphenylacetamido)-3-(4-β-sulfoethylpyridinium)-methyl-3-cephem-4-carboxylic acid·2 Na salt is obtained.

IR Absorbent spectrum (Nujol): $V_{c=o}$ (β-lactam)=1770 cm$^{-1}$ $V_{so2}$(—SO₃H)=1230 cm$^{-1}$, 1045 cm$^{-1}$

| NMR spectrum (D₂O) |
| --- |
| δ 3.37 (s.4H (N 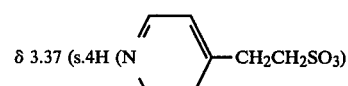—CH₂CH₂SO₃) |
| δ 3.47 (m.2H) (2 position > CH₂) |
| δ 5.10 (d.1H) (6 position - H) |
| δ 5.33 (m.2H) (3 position - CH₂—N 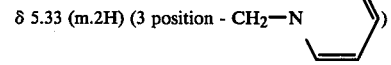) |

-continued

NMR spectrum (D₂O)

δ 5.58 (S.1H) (—CH—) 

δ 5.78 (d.1H) (7 position - H)

δ 6.98 (d.2H)
δ 7.48 (d.2H) 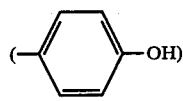 (—⟨ ⟩—OH)

δ 7.90 (m.3H) imidazole 2 position - H + pyridine ring 3.5 position - H

δ 8.78 (d.2H) (pyridine ring 2.6 position - H)

As is evident from the results exemplified above, it can be concluded that the sodium salts of the imidazoledicarboxylic acid derivatives of the present invention can be prepared directly, omitting the unwieldly and inefficient prior art step of preparing the potassium salt and subsequently converting to the sodium salt by cation exchange and treatment with sodium hydroxide.

Having now specifically described this invention, it will be apparent to one of skill in the art that the same is subject to many obvious modifications and variations without affecting or changing the scope thereof.

What is claimed and intended to be secured by Letters Patent in the United States is:

1. A method of preparing sodium salts of imidazoledicarboxylic acid derivatives of substituted cephalosporins having the formula:

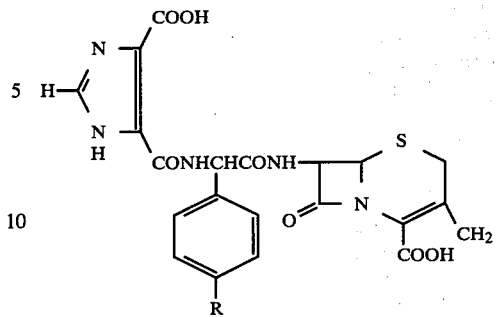

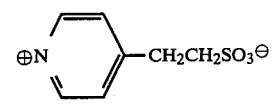

R: H, OH comprising:
reacting a compound of the formula:

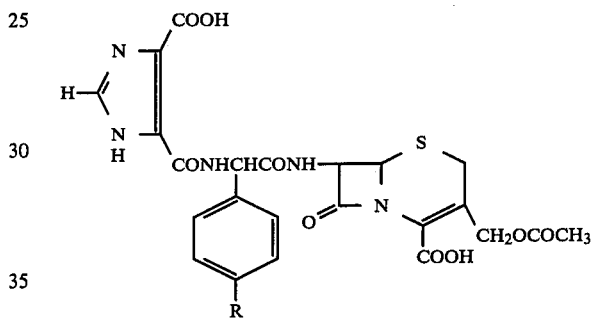

R: H, OH wherein R is hydrogen or hydroxyl, with 4-pyridineethanesulfonic acid in an aqueous solution of sodium iodide at pH 6.0 to 7.5;
contacting the reaction solution with a hydrophilic organic solvent selected from the group consisting of $C_1$-$C_4$ alcohols, acetone, acetonitrile and mixtures thereof to precipitate the sodium salt of the imidazoledicarboxylic acid reaction product; and
separating said precipitated sodium salt from the remainder of the reaction mixture.

2. The method of claim 1, wherein said sodium salt is the mono-sodium salt, the di-sodium salt or mixtures thereof of said imidazoledicarboxylic acid reaction product.

* * * * *